US00PP20723P2

(12) United States Plant Patent
Saul

(10) Patent No.: US PP20,723 P2
(45) Date of Patent: Feb. 9, 2010

(54) ***LAMIUM MACULATUM* PLANT NAMED 'LEMON FROST'**

(50) Latin Name: *Lamium maculatum*
Varietal Denomination: Lemon Frost

(75) Inventor: Richard G. Saul, Cleveland, GA (US)

(73) Assignee: ITSaul Plants, LLC., Alpharetta, GA (US)

( * ) Notice: Subject to any disclaimer, the term of this patent is extended or adjusted under 35 U.S.C. 154(b) by 0 days.

(21) Appl. No.: 12/313,802

(22) Filed: Nov. 25, 2008

(51) Int. Cl.
*A01H 5/00* (2006.01)

(52) U.S. Cl. ..... Plt./444

(58) Field of Classification Search ..... Plt./263, Plt./444

See application file for complete search history.

*Primary Examiner*—Susan B McCormick Ewoldt
(74) *Attorney, Agent, or Firm*—Penny J. Aguirre

(57) ABSTRACT

A new cultivar of *Lamium* plant, 'Lemon Frost', characterized by its foliage that is think in substance and emerges bright yellow-green in color with a white center stripe, by its hardiness in the Southern regions of the U.S., its very vigorous growth habit, and its lavender flowers produced in spring and intermittently throughout the summer.

2 Drawing Sheets

Botanical classification: *Lamium maculatum.*
Variety denomination: 'Lemon Frost'.

BACKGROUND OF THE INVENTION

The present invention relates to a new and distinct cultivar of *Lamium* plant, botanically known as *Lamium maculatum* 'Lemon Frost' and will be referred to hereinafter by its cultivar name, 'Lemon Frost'. The new cultivar of *Lamium* is a hardy herbaceous perennial grown for landscape use.

'Lemon Frost' was discovered by the Inventor in fall of 2000 as a naturally occurring branch mutation of *Lamium maculatum* 'Anne Greenway' (not patented) in his garden in Cleveland, Ga.

Asexual reproduction of the new cultivar was first accomplished by the Inventor by means of stem cuttings in September of 2000. The characteristics of the new cultivar have been found to be stable and reproduced true to type in successive generations.

SUMMARY OF THE INVENTION

The following traits have been repeatedly observed over a period of eight years and represent the characteristics of the new cultivar. These attributes in combination distinguish 'Lemon Frost' as a new and unique cultivar of *Lamium.*

1. 'Lemon Frost' exhibits foliage that emerges bright yellow-green in color with a white center stripe.
2. 'Lemon Frost' exhibits foliage that has a thick substance.
3. 'Lemon Frost' has shown to be hardy in the Southern U.S. regions.
4. 'Lemon Frost' has a very vigorous growth habit.
5. 'Lemon Frost' produces lavender flowers in April and then intermittently throughout the summer in Georgia.

The parent plant, 'Anne Greenway', differs from 'Lemon Frost' is having foliage that is variegated with green and white centers and gold margins and in having a less vigorous growth habit. 'Lemon Frost' can be most closely compared to 'Aurea' (not patented) and 'Beedham's White' (not patented) as they are both similar in having yellow-green foliage. 'Aurea' differs from 'Lemon Frost' in having leaves that are thinner with less distinct venation, in having a poor survival rate in Southern climates and in having a growth rate that is only half as fast as that of 'Lemon Frost'. 'Beedham's White' differs from 'Lemon Frost' in having white flowers and in having a poor survival rate in Southern climates.

BRIEF DESCRIPTION OF THE DRAWINGS

The accompanying colored photographs illustrate the overall appearance and distinct characteristics of the new *Lamium*. The photographs were taken of a three year-old plant as grown outdoors in a three-gallon container in Dahlonega, Ga.

The photograph in FIG. 1 provides an overall view of 'Lemon Frost' in bloom.

Figure 1:
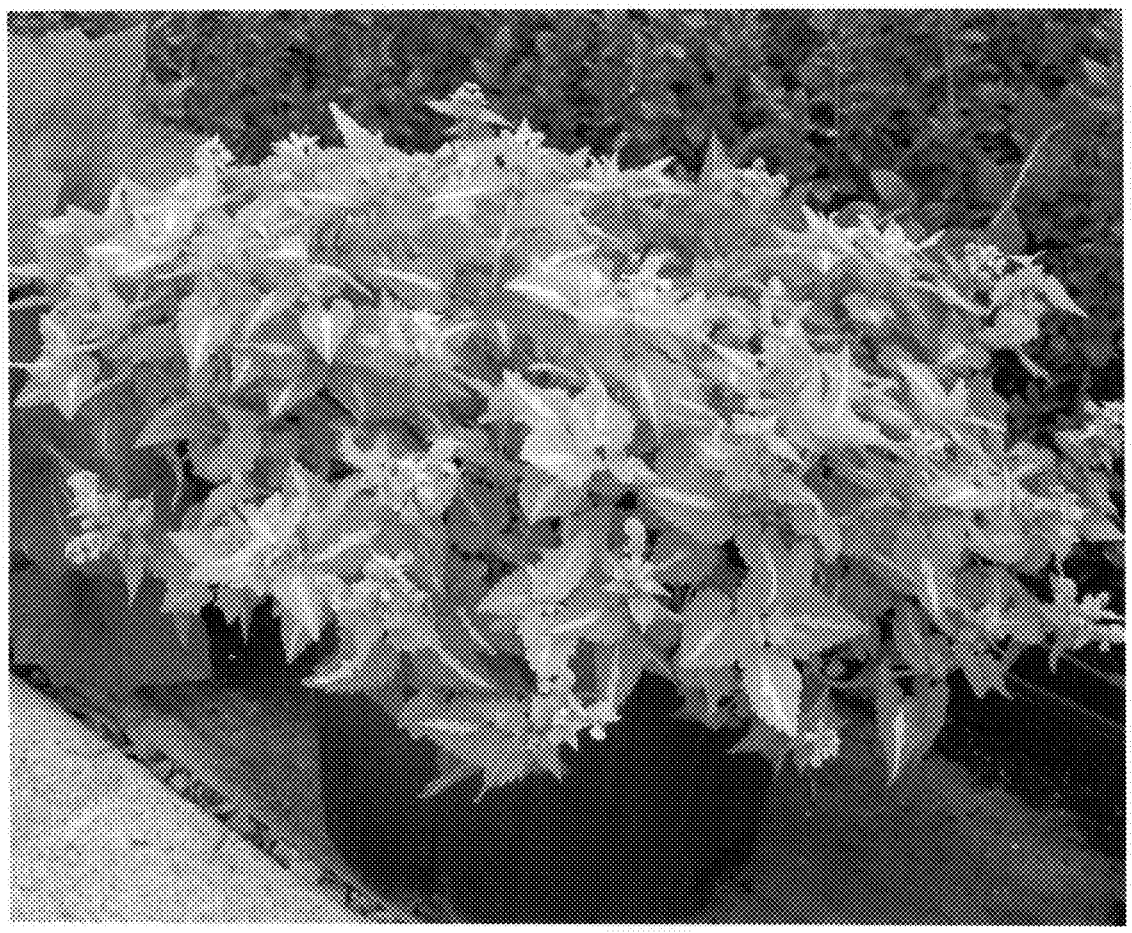
Figure 2:
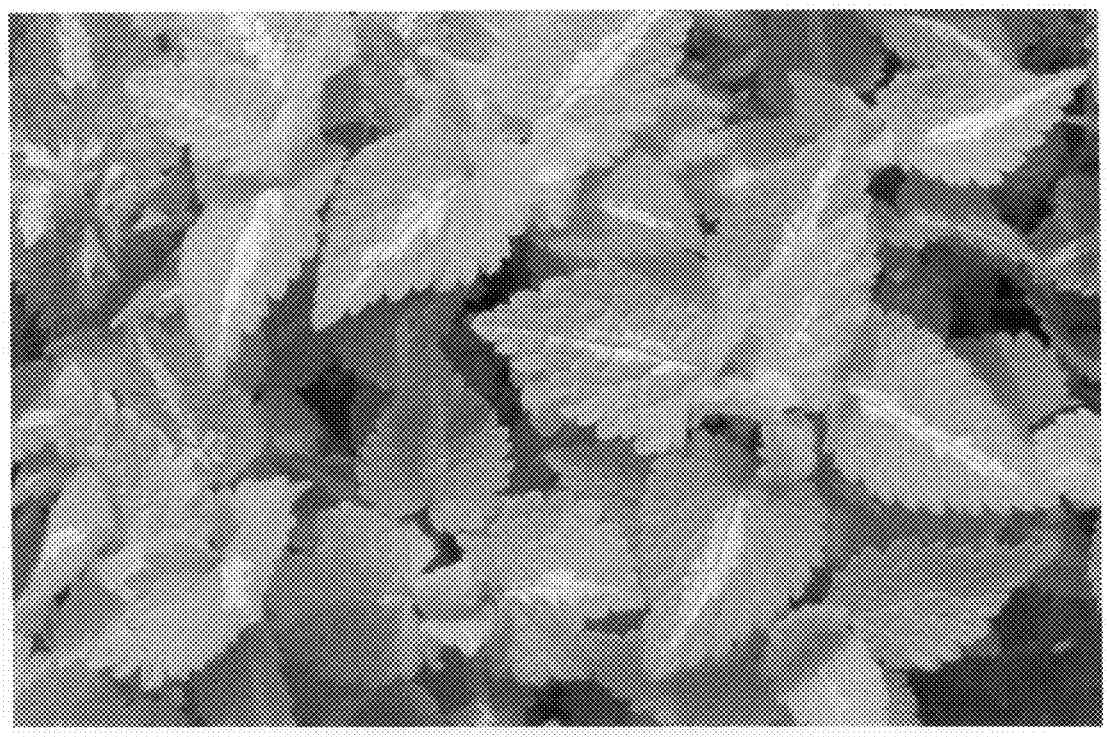

The photograph in FIG. 2 provides a close up view of the foliage of 'Lemon Frost'.

Figure 3:
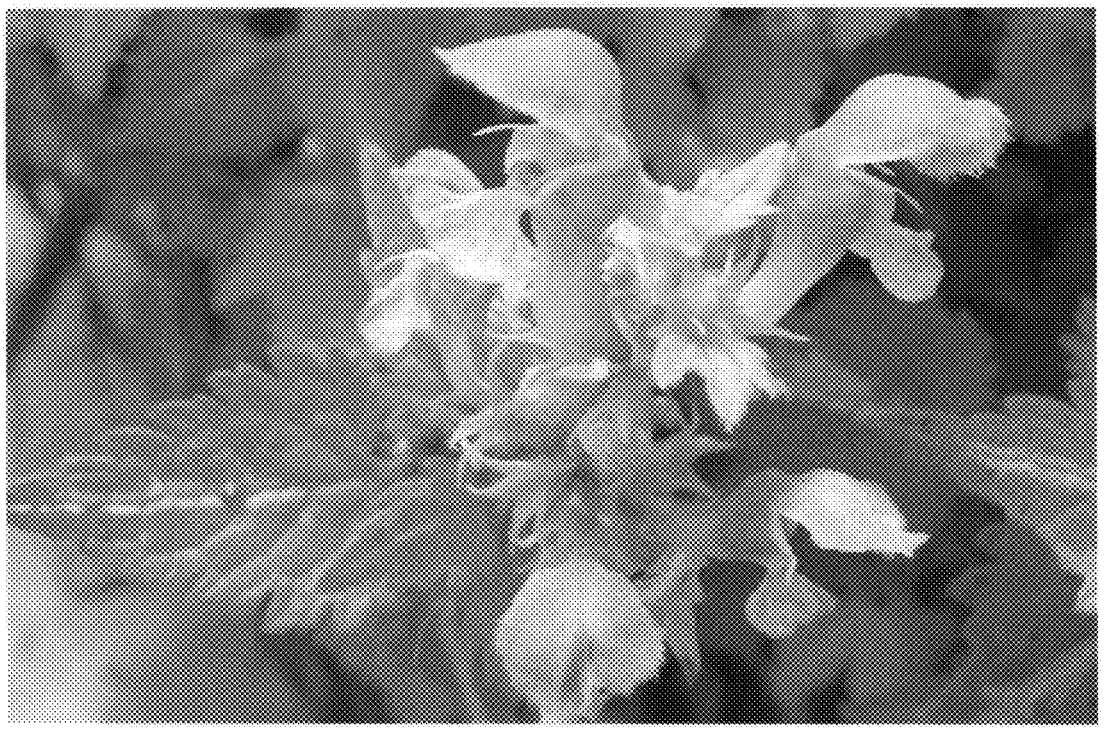

The photograph in FIG. 3 provides a close up view of the flowers of 'Lemon Frost'.

The colors in the photograph may differ slightly from the color values cited in the detailed botanical description, which accurately describe the colors of the new *Lamium.*

DETAILED BOTANICAL DESCRIPTION

The following is a detailed description of the new cultivar as observed for eight years in Georgia with the detailed botanical data collected from a plant grown in a two year-old plant as grown in a one-gallon container grown outdoors in Dahlonega, Ga. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General description:

*Blooming period.*—Blooms heavily in April with intermittent blooms throughout the summer.

*Plant habit*.—Herbaceous perennial, mounded plant habit, flowering stems emerging from basal leaves.

*Height and spread*.—Reaches a height of 15 to 20 cm and a spread of about 60 cm.

*Hardiness*.—U.S.D.A. Zones 4 to 8.

*Culture*.—Has shown to perform well and be very hardy in the Southern U.S. states.

*Diseases and pests*.—No susceptibility or resistance to diseases or pests has been observed.

*Root description*.—Fibrous.

*Propagation*.—Stem cuttings; root initiation occurs in 7 days and a rooted cutting will develop in a 72-cell plug in 14 days during the summer months.

*Growth rate*.—Very vigorous.

Stem description:

*Shape*.—Square.

*Stem color*.—Young; 144B to 144C, mature; 146C becoming heavily suffused with 200A.

*Stem size*.—Average of 3 mm in diameter and 19 cm in length.

*Stem surface*.—Ridged with vertical ridges, sparsely covered with file white hairs about 0.7 mm in length.

*Branching habit*.—Primarily emerge from base with some smaller secondary branches, about, about 14 lateral branches per plant grown in a one-gallon container.

Foliage description:

*Leaf division*.—Simple.

*Leaf arrangement*.—Opposite.

*Leaf shape*.—Ovate.

*Leaf size*.—Variable with new leaves emerging from nodes, mature leaves average 4.5 cm in length and 3 cm in width.

*Leaf number*.—Average of 40 per stem 19 cm in length.

*Leaf base*.—Cordate.

*Leaf apex*.—Acute to acuminate.

*Leaf margin*.—Crenate, about 18 per side on leaf 4.5 cm in length, densely covered with fine hairs.

*Leaf venation*.—Reticulate, recessed on upper surface and raised on lower surface, color matches leaf color.

*Leaf surface*.—Upper surface; sparsely covered with fine hairs, lower surface; puberulent sparsely covered with fine hairs.

*Leaf substance*.—Thick in comparison to most other cultivars of *Lamium*.

*Leaf internode length*.—Average of 2 cm.

*Leaf variegation pattern*.—A vertical stripe of white in center surrounded by yellow-green margins.

*Leaf color*.—Newly formed upper and lower surface; blend of N144B and 150B without variegation and developing centers that are 157D on upper surface and 145A on lower surface, mature upper surface; margin a blend of 144A and 138A and center 159C, mature lower surface; a blend of 144A and 138B.

*Petiole*.—Average of 1 cm in length and 1.5 mm in length, N144A in color on young leaves and 144A in color on mature leaves, surface is covered with fine white hairs.

*Foliage fragrance*.—Slightly mint-like when crushed.

Flower description:

*Inflorescence type*.—Verticillasters (dense whorls) of galeate flowers.

*Lastingness of inflorescence*.—Individual flowers last 3 to 4 days, inflorescence lasts about 10 days.

*Inflorescence size*.—Verticillasters are about 3.2 cm in diameter and 2.2 cm in diameter.

*Flower type*.—Zygomorphic and galeate.

*Flower number*.—About 6 to 7 flowers per verticillaster produced on upper axillary nodes.

*Flower fragrance*.—Pungent (typical of species).

*Flower buds*.—Petal portion is globose in shape, about 1.2 mm in length and 5 mm in diameter, color 77A with tube portion 149D and calyx portion same as open flower.

*Flower size*.—About 2.5 cm in length and about 1.3 cm in diameter.

*Peduncles*.—None, sessile.

*Calyx*.—5-pointed, star-shaped, divergent, about 6 mm in length and 7 mm in width, persistent.

*Sepals*.—5, primarily fused with un-fused portion somewhat spreading with free portion about 2 mm in width and 3 mm in length, 160B in color with shading of 187D and apex 144C, surface is glabrous with apex villose, base is fused, apiculate apex, entire margin.

*Petals*.—2 lipped with upper lip; galeate and curved like a hood, broadly obovate in shape with a round apex, base is truncate and fused to lower lip, margin is entire and pubescent, color of outer surface is a blend of 77A and 77B and inner surface a blend of 76A and 76B, 1.3 cm in height and 1 cm in width, lower lip; fused into tube at base with 2 lateral lobes and a front lobe having two kidney-shaped sections that downward, lateral lobes are about 6 mm in length and diameter, pubescent surface, margin is entire with a linear appendage about 2 mm in length and 0.3 mm in width on each lateral lobe, color is a blend of 77A and 77B on the outer surface and a blend of 76A and 76B on inner surface, front lobe has a glabrous surface, entire margins, are kidney shaped, about 2 mm in height and 3 mm in width and color is NN1D with speckles of 77A, tube; 4 mm in length and 3 mm in width, glabrous and satiny surface and NN1C in color.

Reproductive organs:

*Gynoecium*.—1 Pistil, style is about 1.5 cm in length, 0.3 mm in width and 155C in color, stigma is bi-fid with and NN155C in color, ovary is superior, about 1.5 mm in diameter and 195B in color in color.

*Androecium*.—4 stamens, filament is about 1. cm in length, 0.3 mm in width, adnate to corolla and NN155C in color, anthers are oblong in shape, about 1.2 mm in length, attachment is basifixed, margins are villose and N200A in color, pollen is abundant and 163B in color.

*Fruit*.—Fruit and seed production was not observed under the conditions tested.

It is claimed:

1. A new and distinct variety of *Lamium* plant designated 'Lemon Frost' as described and illustrated herein.

* * * * *